United States Patent [19]

Lisowsky

[11] Patent Number: 5,453,221
[45] Date of Patent: Sep. 26, 1995

[54] BRIDGED CYCLOPENTADIENYLMAGNESIUM COMPOUNDS AND USE THEREOF FOR PREPARING METALLOCENES

[75] Inventor: Richard Lisowsky, Kamen, Germany

[73] Assignee: Witco GmbH, Bergkamen, Germany

[21] Appl. No.: 392,387

[22] Filed: Feb. 22, 1995

[30] Foreign Application Priority Data

Feb. 25, 1994 [DE] Germany ............... 44 06 110.2

[51] Int. Cl.$^6$ ............... C07F 7/08; C07F 7/10; C07F 3/02
[52] U.S. Cl. ............... 260/665 G; 556/413; 556/445; 556/447; 556/465; 556/466; 556/487; 556/404; 564/305; 564/306; 564/307; 564/457; 568/8; 568/9; 568/584; 568/630; 568/631; 568/664
[58] Field of Search ............... 556/413, 445, 556/447, 465, 466, 487, 404; 564/305, 306, 307, 457; 568/8, 9, 584, 630, 631, 664

[56] References Cited

U.S. PATENT DOCUMENTS

| | | | |
|---|---|---|---|
| 4,447,369 | 5/1984 | Ashby | 260/665 R |
| 5,231,205 | 7/1993 | Rieke | 260/665 R |
| 5,359,105 | 10/1994 | Strickler et al. | 556/410 |

FOREIGN PATENT DOCUMENTS

| | | |
|---|---|---|
| 622826 | 8/1990 | Australia. |
| 0344887A2 | 3/1989 | European Pat. Off.. |
| 0416815A2 | 8/1990 | European Pat. Off.. |
| 0420436A1 | 9/1990 | European Pat. Off.. |
| 0530908A1 | 1/1992 | European Pat. Off.. |
| 0520732A1 | 6/1992 | European Pat. Off.. |
| 0480390A2 | 9/1991 | Germany. |
| 4402192 | 9/1992 | Germany. |

OTHER PUBLICATIONS

Elsevier Sequoia S. A., Lausanne, *Journal of Organometallic Chemistry*, X–Ray structures of ethylenebis (tetrahydroindenyl)–titianium and –zirconium dichlorides: a revision; (1988) pp. 21–29.

*Primary Examiner*—Paul F. Shaver
*Attorney, Agent, or Firm*—Scully, Scott, Murphy & Presser

[57] ABSTRACT

Disclosed are new bridged cyclopentadienylmagnesium compounds of the general formula Q(CpR$_a$) (Cp'R'$_a$.)Mg, processes for the preparation thereof, and the use thereof for preparing bridged metallocenes.

2 Claims, No Drawings

BRIDGED CYCLOPENTADIENYLMAGNESIUM COMPOUNDS AND USE THEREOF FOR PREPARING METALLOCENES

BACKGROUND OF THE INVENTION

The present invention relates to new bridged copentadienylmagnesium compounds of the general formula $Q(CpR_a)(Cp'R'_{a'})Mg$, processes for the preparation thereof and also their use for preparing bridged metallocenes.

BRIEF SUMMARY OF THE INVENTION

In one aspect of the present invention, compounds of the general formula $Q(CpR_a)(Cp'R'_{a'})Mg$ are prepared by reaction of bridged cyclopentadienyl compounds in accordance with the equation $$Q(CpR_a)(Cp'R'_{a'}) + (R^3R^4)_cMg \rightarrow Q(CpR_a)(Cp'R'_{a'})Mg + cR^3H + cR^4H.$$

Another aspect of the present invention is compounds of the general formula (1)

$$Q(CpR_a)(Cp'R'_{a'})Mg \qquad (1)$$

In the foregoing equation and in formula (1), Cp is a cyclopentadienyl or an indenyl radical;

R and R' are each an alkyl, phosphine, amino, alkylamino, dialkylamino, alkoxy, alkoxy-alkyl, arylalkyl, or aryloxy-alkyl group with $0 \leq a \leq 4$ and $0 \leq a' \leq 4$;

Cp' is one of the groups Cp, or when a' is 1, Cp'R' an be NR" wherein R" is a $C_1$–$C_{12}$ alkyl or $C_6$–$C_{10}$ aryl radical; and Q is a single-membered or multi-membered bridge between Cp and Cp', wherein $$Q \text{ is } (R^1—Z—R^2)_b,$$

wherein $R^1$ and $R^2$ are identical or different and each is a hydrogen atom, a $C_1$–$C_{10}$-alkyl group or a $C_6$–$C_{10}$-aryl group; Z is carbon, silicon or germanium; and b is 1, 2 or 3.

Referring to the R and R' substituents, each one can be alkyl containing 1 to 10 carbon atoms, for example methyl (including dimethyl and trimethyl);

alkoxy containing 1 to 10 carbon atoms, for example methoxy (including dimethoxy and trimethoxy);

alkoxylamino and/or dialkylamino, wherein each alkyl group contains 1 to 10 carbon atoms, for example dimethylamino and dipropylamino (including bis(dimethylamino));

alkoxyalkyl containing a total of 2 to 20 carbon atoms;

aryl-alkyl and/or aryloxy-alkyl groups wherein the aryl group contains 6 to 10 carbon atoms and the alkyl portion contains 1 to 10 carbon atoms;

phosphine, including phosphine substituted with 1 or 2 groups each of which is $C_1$–$C_{10}$ alkyl or $C_6$–$C_1$–$C_{10}$ aryl, for example diphenylphosphino.

DETAILED DESCRIPTION OF THE INVENTION

Examples of the bridged biscyclopentadienyl compounds $Q(CpR_a)(Cp'R'_{a'})$ which can be used according to the invention in the reaction equation set forth above are dimethylsilylbis(1-indene), dimethylsilylbis(1-cyclopentadiene), 2,2-propylbis(1-indene), 2,2-propylbis(trimethylcyclopentadiene), 2,2-propylbis(5-dimethylamino-1-indene), 2,2-propylbis(6-dipropylamino-1-indene), 2,2-propylbis(4,7-bis(dimethylamino-1-indene)), 2,2-propylbis(5-diphenylphosphino-1-indene), 2,2-propylbis(4,5,6,7-tetrahydro-1-indene), 2,2-propylbis(4-methyl-1-indene), 2,2-propylbis(5-methyl-1-indene), 2,2-propylbis(6-methyl-1-indene), 2,2-propylbis(7-methyl-1-indene), 2,2-propylbis(5-methoxy-1-indene), 2,2-propylbis(4,7-dimethoxy-1-indene), 2,2-propylbis(2,3-dimethyl-1-indene), 2,2-propylbis(4,7-dimethyl-1-indene), 2,2-propylbis(1-cyclopentadiene), 2,2-propylbis(1-indene)(1-cyclopentadiene), diphenylmethylbis(1-indene), diphenylmethylbis(1-cyclopentadiene), diphenylmethylbis(1-indene), diphenylmethylbis(1-indene)(1-cyclopentadiene), diphenylsilylbis(1-indene), diphenylsilylbis(1-cyclopentadiene), diphenylsilylbis(1-indene) (1-cyclopentadiene), ethylenebis(1-indene), ethylenebis(trimethylcyclopentadiene), ethylenebis(5-dimethylamino-1-indene), ethylenebis(6-dipropylamino-1-indene), ethylenebis(4,7-bis(dimethylamino)-1-indene), ethylenebis(5-diphenylphosphino-1-indene), ethylenebis(4,5,6,7-tetrahydro-1-indene), ethylenebis(4-methyl-1-indene), ethylenebis(5-methyl-1-indene), ethylenebis(6-methyl-1-indene), ethylenebis(7-methyl-1-indene), ethylenebis(5-methoxy-1-indene), ethylenebis(4,7-dimethoxy-1-indene), ethylenebis(2,3-dimethyl-1-indene), ethylenebis(4,7-dimethyl-1-indene), ethylenebis(9-fluorene), ethylenebis(1-cyclopentadiene), ethylenebis(1-indene), ethylenebis(1-indene)(1-cyclopentadiene), dimethylsilylbis(1-indene), and dimethylsilylbis(1-indene)(1-cyclopentadiene).

These compounds belong to the known state of the art and are described in EP-A-0 480 390, EP-A-0 413 326, EP-A-0 530 908, EP-A-0 344 887, EP-A-0 420 436, EP-A0 416 815, and/or EP-A-0 520 732. They can be prepared by the processes described in these documents and also in DE-A-44 02 192.

The one or more compounds $(R^3R^4)_cMg$ used in the reaction equation set forth above are those in which $R^3$ and $R^4$ are each bonded to the Mg and are each identical or different and are H or $C_{1-12}$-alkyl radicals; and c is 0 or 1, preferably 1. According to the invention, preference is given to butylethylmagnesium, di-n-butylmagnesium, di-n-hexylmagnesium, and n-butyl-sec-butylmagnesium in their commercial formulations, and in particular, BOMAG®-A from Witco GmbH (a mixture of di-octylmagnesium, di-butylmagnesium, and optionally octylbutylmagnesium, wherein the ratio of butyl to octyl substituents is 3:1, 20% strength in heptane). In the case that the one or more compounds $(R^3R^4)_cMg$ are supplied in a solvent, no additional solvent is required for carrying out the reaction. The progress of the reaction can be monitored by means of the gas evolution.

The starting materials are preferably used in stoichiometric amounts.

The reactions are carried out in an inert gas atmosphere and with exclusion of oxygen and moisture. In these reactions, according to the invention, the components are preferably initially charged at room temperature in an inert solvent and the temperature is raised while stirring vigorously.

The inert solvents which can be used are those which are customary in this field, such as, for example, aliphatic and/or cyclic ethers or aliphatic and/or aromatic hydrocarbons.

According to the invention, preference is given to aliphatic hydrocarbons having boiling points $\geq 60°$ C., preferably $\geq 80°$ C., in particular in the range of $80°$–$120°$ C. To achieve practical reaction times, the reaction is preferably carried out at the boiling point of the solvent, in particular between 80°–120° C. The amount of solvent is largely non-critical; however, to achieve higher space-time yields, the reaction is carried out in the upper technically possible region.

One aspect of the invention is accordingly compounds of the general formula (1)

$$Q(CpR_a)(Cp'R'_{a'})Mg \qquad (1)$$

wherein

Cp is a cyclopentadienyl or an indenyl radical;

R and $R^1$ are each an alkyl, phosphine, amino, alkylamino, dialkylamino, alkoxy, alkoxy-alkyl, aryl-alkyl or aryloxy-alkyl group with $0 \leq a \leq 4$ and $0 \leq a' \leq 4$;

Cp' is one of the groups Cp or when a' is 1,

Cp' can be NR" wherein R" is a $C_1$–$C_{12}$ alkyl or $C_6$–$C_{10}$ aryl radical, and wherein Q is a single-membered or multi-membered bridge between Cp and Cp', wherein Q is $$(R^1-Z-R^2)_b,$$

wherein $R^1$ and $R^2$ are identical or different and each is a hydrogen atom, a $C_1$–$C_{10}$-alkyl group or a $C_6$–$C_{10}$-aryl group, Z is carbon, silicon or germanium, and b is 1, 2 or 3.

A further aspect of the subject matter of the invention is a process for preparing one or more compounds of the general formula $Q(CpR_a)(Cp'R'_{a'})Mg$, where Q, Cp, R, Cp', R', a and a' are as specified herein; by reaction of one or more bridged cyclopentadienyl compounds of the general formula $Q(CpR_a)(Cp'R'_{a'})$ in the presence of an inert solvent with one or more magnesium compounds $(R^3R^4)_cMg$, where $R^3$ and $R^4$ are, independently of one another, H or $C_1$–$C_{12}$-alkyl radicals and c is 0 or 1.

Further subject matter of the present invention is characterized by the claims herein.

The compounds of the invention of the general formula (1) $Q(CpR_a)(Cp'R'_{a'})Mg$ are valuable starting materials for the preparation of metallocenes. For the purposes of the present invention, the term "metallocenes" includes both sandwich complexes and semi-sandwich complexes.

These metallocenes are prepared by reaction of one or more compounds of the general formula (1) with one or more compounds of the general formula $M(X)_m$, where M is a transition metal in any of the groups 3 to 8 of the Periodic Table of the Elements (IUPAC notation), in particular Sc, Ti, Zr, Hf or Fe; m is the numerical value of the oxidation state of M in said compound $M(X)_m$; and X is a halogen, in particular Cl or Br.

The reaction is advantageously carried out in the presence of one or more inert ethers such as aliphatic, cycloaliphatic and/or aromatic ethers such as diethyl ether, methyl tert-butyl ether, tetrahydrofuran, dimethoxyfuran, or dimethoxyethane; or inert aliphatic and/or aromatic hydrocarbons such as hexane, heptane, octane, toluene, or xylene.

Preference is given to ethers and hydrocarbons in which the final products are soluble.

The mixing of the reactants can be carried out in a manner similar to that of the process described in EP-A-0 420 436 and EP-A-0 416 815.

However, according to the invention, the process is preferably carried out by initially charging the transition metal halide $M(X)_m$ in an ether or an aromatic hydrocarbon and directly, i.e. without previous workup and isolation, metering in the reaction mixture formed in the preparation of the compounds of the formula (1) in preferably stoichiometric amounts. The reaction temperature is selected as a function of the starting compound and can be between about −70° C. and about 120° C. According to the invention, preference is given to temperatures from −20° to +20° C.

The workup is carried out by separating off the magnesium salts which form upon reaction of the compound or compounds of formula (1) with the halide $M(X)_m$ and isolating the metallocene in a conventional manner by processes known in this field.

EXAMPLES

All experiments were carried out with exclusion of oxygen and moisture under inert gas.

Example 1

Preparation of ethylenebis(indenyl)magnesium:

10 g of indene (95% strength; 82 mmol) were mixed with 34.2 g of BOMAG®-A (20% strength in heptane; 41 mmol) in a 100 ml glass flask at room temperature and subsequently heated for 4 hours under reflux.

7.7 g (41 mmol) of 1,2-dibromoethane and 5.3 g (41 mmol) of di-n-butyl ether were then added at room temperature and the mixture was again stirred for 3 hours under reflux.

The solution of ethylenebis(indenyl) thus prepared was subsequently freed of precipitated $MgBr_2$ by means of filtration.

The filtrate was admixed with 34.2 g of BOMAG®-A (20% strength in heptane; 41 mmol) and refluxed for 4 hours.

It was cooled to −10° C. and filtered.

The filter residue was dried in vacuo (100° C./0.1 mbar).

11.3 g (98% of theory) of a colorless solid was isolated. Ethylenebis(indenyl)magnesium:

Mg: (calc.: 8.66%) found: 8.56% $^1$H-NMR: (DMSO) 7.2 (m, 2H); 7.0 (m, 2H); 6.4 (d, 2H); 6.2 (m, 4H); 5.6 (d, 2H); 3.0 (s, 4H).

Example 2

Preparation of dimethylsilylbis(indenyl)magnesium:

12.2 g of indene (95% strength; 0.1 mol) were admixed with 42 g of BOMAG®-A (20% strength in heptane; 50 mmol) at room temperature and then refluxed for 4 hours. 6.45 g of $Me_2SiCl_2$ (50 mmol) and 6.5 g of di-n-butyl ether (50 mmol) were subsequently added at room temperature and the mixture was again refluxed for 2 hours.

After filtration, the filtrate, which contained dimethylbis-(indenyl)silane, was admixed with a further 42 g of BOMAG®-A and refluxed for 2 hours.

The mixture was then cooled to −20° C. and the precipitated solid was isolated and dried at 100° C./0.1 mbar.

15.1 g (97% of theory) of a white solid was isolated.

$Me_2Si(indenyl)_2Mg$: Mg: (calc.: 7.8%) found: 7.75% $^1$H-NMR: (DMSO) 7.4 (d, 2H); 7.1 (d, 2H); 6.65 (d, 2H); 6.25 (t, 2H); 6.15 (t, 2H); 5.8 (d, 2H); 0.4 (s, 6H)

Example 3 a: Preparation of $Me_2Si[(Me_4Cp)(N-t-Bu)]Mg$:

10 g (40 mmol) of $Me_2Si[(Me_4CpH)(t-BuNH)]$ (Reference: Organometallics, 1990, 9, 867) were added at room temperature to 48 ml of BOMAG®-A (40 mmol) and the mixture was refluxed for 3 hours. The solution was subsequently cooled to −40° C. and the precipitated solid was isolated (10.5 g; 99% of theory).

Mg: (calc. 8.9%) found: 8.7% $^1$H-NMR: (DMSO) 1.99 (s, 6H, Me$_2$Cp); 1.79 (s, 6H, Me$_2$Cp); 1.09 (s, 9H, Me$_3$C); 0.12 (s, 6H, Me$_2$Si)

b: Preparation of Me$_2$Si[(Me$_4$Cp)(t-BuN)]ZrCl$_2$ 12 g (48 mmol) of Me$_2$Si[(Me$_4$CpH)(t-BuNH)] were added at room temperature to 40 g of BOMAG®-A (1.2 mol/kg; 48 mmol), initially charged in a 250 ml glass flask, and the mixture was refluxed for 2 hours. This freshly prepared solution was quickly introduced into a suspension of 11.2 g of ZrCl$_4$ (48 mmol) in 150 ml of diethyl ether at −20° C. After the mixture had been warmed to room temperature over a period of 1 hour, it was refluxed for a further 1 hour. The magnesium salt which precipitated was subsequently filtered off, and the clear filtrate was evaporated to 40 ml and cooled to −20° C. 15.8 g of Me$_2$Si[(Me$_4$Cp)(t-BuN)]ZrCl$_2$ (38.4 mmol; 80% of theory) were isolated.

$^1$H-NMR (CDCl$_3$): 0.62 (s,6H, Me$_2$Si); 1.4 (s, 9H, Me$_3$C); 2.12 (s, 6H, Me$_2$Cp); 2.2 ppm (s, 6H, Me$_2$Cp).

What is claimed is:

1. A compound of the general formula (1)

$$Q(CpR_a)(Cp'R'_{a'})Mg \qquad (1)$$

wherein

Cp is a cyclopentadienyl or an indenyl radical;

R and R' are the same or different and each is selected from the group consisting of alkyl, phosphine, amino, alkylamino, dialkylamino, alkoxy, alkoxy-alkyl, arylalkyl, and aryloxy-alkyl groups; $0 \leq a \leq 4$ and $0 \leq a' \leq 4$;

Cp' is cyclopentadienyl or indenyl, or when a' is 1, Cp'R' can be NR" wherein R" is a C$_1$–C$_{12}$ alkyl or a C$_6$–C$_{10}$ aryl radical; and Q is a single-membered or multi-membered bridge between Cp and Cp' and represents $$(R^1-Z-R^2)_b,$$

wherein R$^1$ and R$^2$ are identical or different and each is a hydrogen atom, a C$_1$–C$_{10}$ alkyl group or a C$_6$–C$_{10}$-aryl group; Z is carbon, silicon or germanium; and b is 1, 2 or 3.

2. A compound according to claim 1 wherein Cp'R'$_{a'}$ is NR".

* * * * *